US012752062B2

(12) United States Patent
Yin

(10) Patent No.: US 12,752,062 B2
(45) Date of Patent: Oct. 6, 2026

(54) SUB-ASSEMBLY FOR A MEDICAMENT DELIVERY DEVICE CASSETTE UNIT

(71) Applicant: SHL MEDICAL AG, Zug (CH)

(72) Inventor: Ming-Ting Yin, Taipei City (TW)

(73) Assignee: SHL Medical AG, Zug (CH)

( * ) Notice: Subject to any disclaimer, the term of this patent is extended or adjusted under 35 U.S.C. 154(b) by 653 days.

(21) Appl. No.: 18/038,795

(22) PCT Filed: Dec. 3, 2021

(86) PCT No.: PCT/EP2021/084082

§ 371 (c)(1),
(2) Date: May 25, 2023

(87) PCT Pub. No.: WO2022/128520

PCT Pub. Date: Jun. 23, 2022

(65) Prior Publication Data

US 2024/0001042 A1 Jan. 4, 2024

Related U.S. Application Data

(60) Provisional application No. 63/191,355, filed on May 21, 2021.

(30) Foreign Application Priority Data

Dec. 16, 2020 (EP) .................................... 20214480

(51) Int. Cl.
*A61M 5/32* (2006.01)

(52) U.S. Cl.
CPC .................................. *A61M 5/326* (2013.01)

(58) Field of Classification Search
CPC ........ A61M 5/2033; A61M 2005/2013; A61M 2005/208; A61M 2205/581;
(Continued)

(56) References Cited

U.S. PATENT DOCUMENTS

RE44,640 E 12/2013 Heiniger
8,932,254 B2 1/2015 Eaton
(Continued)

FOREIGN PATENT DOCUMENTS

EP 1267966 B1 11/2005
EP 1542744 B1 6/2009
(Continued)

OTHER PUBLICATIONS

International Search Report and Written Opinion for Int. App. No. PCT/EP2021/084082, mailed Mar. 1, 2022.

*Primary Examiner* — Michael J Tsai
*Assistant Examiner* — Kathleen Paige Vokes
(74) *Attorney, Agent, or Firm* — McDonnell Boehnen Hulbert & Berghoff LLP

(57) ABSTRACT

A sub-assembly for a medicament delivery device cassette unit, the sub-assembly having a body extending along a longitudinal axis from a proximal end to a distal end; a delivery member guard coaxially attached to the body and being axially movable relative to the body along the longitudinal axis; a latch adjacent to the delivery member guard and axially movable relative to the body; and a lock member attached to the body; the lock member is movable relative to the latch between a locked position and an unlocked position; the lock member has a distally directed surface facing a proximally directed surface of the latch in the locked position; and wherein the distally directed surface of the lock member is further apart from the proximally directed surface of the latch in the unlocked position than in the locked position.

17 Claims, 10 Drawing Sheets

(58) Field of Classification Search
CPC ................ A61M 5/3157; A61M 5/326; A61M 2005/3142; A61M 2205/276; A61M 2205/582; A61M 5/3129; A61M 5/3243; A61M 5/3275; A61M 2005/2073; A61M 2005/3247; A61M 2005/3267; A61M 5/20
See application file for complete search history.

(56) References Cited

U.S. PATENT DOCUMENTS

| | | | | |
|---|---|---|---|---|
| 9,757,521 | B2 | 9/2017 | McLoughlin et al. | |
| 10,300,213 | B2 | 5/2019 | Bengtsson et al. | |
| 10,561,793 | B2 | 2/2020 | Finke et al. | |
| 10,874,800 | B2 | 12/2020 | Schader et al. | |
| 2005/0203466 | A1 | 9/2005 | Hommann et al. | |
| 2007/0021718 | A1 | 1/2007 | Burren et al. | |
| 2011/0202011 | A1* | 8/2011 | Wozencroft | A61M 5/31505 |
| 2013/0324934 | A1* | 12/2013 | Holmqvist et al. | A61M 5/3202 |
| 2015/0202367 | A1 | 7/2015 | Plaschkes et al. | |
| 2015/0273161 | A1 | 10/2015 | Bengtsson et al. | |
| 2016/0354556 | A1 | 12/2016 | Zucker et al. | |
| 2018/0161504 | A1 | 6/2018 | Kemp et al. | |
| 2018/0169338 | A1 | 6/2018 | Mosebach et al. | |
| 2018/0353709 | A1 | 12/2018 | Schader et al. | |
| 2019/0134315 | A1 | 5/2019 | Moser et al. | |
| 2020/0129699 | A1 | 4/2020 | Helmer | |
| 2020/0316311 | A1* | 10/2020 | Holland et al. | A61M 5/178 |
| 2020/0376200 | A1 | 12/2020 | Zucker et al. | |

FOREIGN PATENT DOCUMENTS

| | | | |
|---|---|---|---|
| EP | 2021054 | B1 | 3/2010 |
| EP | 2346552 | B1 | 8/2012 |
| EP | 2875838 | B1 | 4/2017 |
| EP | 2892590 | B1 | 1/2018 |
| EP | 2331175 | B1 | 4/2018 |
| EP | 3151886 | B1 | 4/2018 |
| EP | 3360591 | A1 | 8/2018 |
| EP | 2879736 | B1 | 11/2018 |
| EP | 3038681 | B1 | 11/2019 |
| EP | 3569271 | A1 | 11/2019 |
| WO | 2004/028598 | A1 | 4/2004 |
| WO | 2009/094793 | A1 | 8/2009 |
| WO | 2015/028393 | A1 | 3/2015 |
| WO | 2016/193341 | A1 | 12/2016 |
| WO | 2016/193355 | A1 | 12/2016 |
| WO | 2019/086443 | A1 | 5/2019 |
| WO | 2019/122946 | A1 | 6/2019 |
| WO | 2020/016166 | A1 | 1/2020 |
| WO | 2020/070327 | A1 | 4/2020 |
| WO | 2020/104812 | A1 | 5/2020 |
| WO | 2020/169842 | A1 | 8/2020 |

* cited by examiner

SUB-ASSEMBLY FOR A MEDICAMENT DELIVERY DEVICE CASSETTE UNIT

CROSS REFERENCE TO RELATED APPLICATIONS

The present application is a U.S. National Phase Application pursuant to 35 U.S.C. § 371 of International Application No. PCT/EP2021/084082 filed Dec. 3, 2021, which claims priority to European Patent Application No. 20214480.4 filed Dec. 16, 2020 and U.S. Provisional Patent Application No. 63/191,355, filed May 21, 2021. The entire disclosure contents of these applications are herewith incorporated by reference into the present application.

TECHNICAL FIELD

The present disclosure generally relates to sub-assemblies for medicament delivery device cassette units such as reusable autoinjectors or injectors with two detachable parts, and particularly to sub-assemblies for locking a delivery member guard of such medicament delivery device cassette units before use.

BACKGROUND

Medicament delivery devices such as pen type manual injectors or auto-injectors are generally known for the self-administration of a medicament by patients without formal medical training. For example, patients suffering from diabetes may require repeated injections of insulin, or patients may require regular injections of other types of medicaments, such as a growth hormone.

Some medicament delivery devices have two parts which are interconnected during use. One part often receives a medicament container which contains a medicament, such as a cartridge or medicament container; this part usually can be called a cassette. The other part often comprises a driver for actuating expelling the medicament.

Medicament delivery devices designed in this way are commonly reusable. The cassette is a disposable part, and the other part with the driver usually is a reusable part. The driver may comprise a power unit such as a spring or a motor and thus can be re-used for a number of medicament deliveries.

Medicament delivery devices are commonly designed to comprise a delivery member guard, for protecting a delivery member (such as a needle or a spray nozzle) for delivering the medicament to the end user from contamination; and for protecting the end user from being injured by the medicament delivery member.

It is common to find a locking mechanism/device for locking the delivery member guard to prevent a distal movement of the delivery member guard after use, usually locking the delivery member guard in the final, used position. Before use, the delivery member guard is often protected by a cap to stop the user from accidentally pushing the delivery member guard and exposing the medicament delivery member. It has been appreciated, however, that alternative solutions for medicament delivery member protection before use could be advantageous.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "radial", "radially", "rotation", "rotational" and "rotationally" refer to a direction generally perpendicular to the longitudinal direction and at least partially extending around the longitudinal direction.

There is hence provided a sub-assembly for a medicament delivery device cassette unit, the sub-assembly comprising: a body extending along a longitudinal axis from a proximal end to a distal end; a delivery member guard coaxially attached to the body and being axially movable relative to the body along the longitudinal axis; a latch adjacent to the delivery member guard and axially movable relative to the body; and a lock member attached to the body; wherein the lock member is movable relative to the latch between a locked position and an unlocked position; wherein the lock member comprises a distally directed surface facing a proximally directed surface of the latch in the locked position; and wherein the distally directed surface of the lock member is further apart from the proximally directed surface of the latch in the unlocked position than in the locked position.

The sub-assembly provided by this present disclosure therefore can releasably prevent the medicament delivery guard from moving relative to the body by positioning the lock member in the locked position or the unlocked position.

In one embodiment, the latch is unidirectionally attached to the delivery member guard. That is, the latch is only axially attached to the delivery member guard when moving in the proximal direction. In this example, the delivery member guard is axially immovable relative to the latch when moving in the proximal direction, meaning that the delivery member guard can only axially move relative to the body together with the latch in the proximal direction.

The proximal movement of the delivery member guard can be therefore used to trigger another action of the medicament delivery device, e.g. priming, needle mounting, or in some cases as a second safety design. For example, there may be a safety mechanism of the delivery member guard on the cassette with the delivery member guard and the delivery member. Such safety mechanism is designed to prevent the delivery member guard from moving in the distal position before use until the cassette of the medicament delivery device has been properly assembled to the other part of the medicament delivery device, so the end user will not accidentally get an injury or contaminate the delivery member. However, when the end user assembles two parts of the medicament delivery device together, sometimes the end user may press on the delivery member guard in the distal direction; and once the safety mechanism being release, the end user may contact the delivery member because the delivery member guard just suddenly move in the distal direction. In such case, the proximal movement of the delivery member guard can be a second safety design, like the delivery member guard cannot move in the distal direction unless the delivery member guard moves into a proximal position first; so that even the end user pressed on the delivery member guard during assembling the two parts of the medicament delivery device together, the delivery member guard will not able to be moved in the distal direction unless (i) it has been properly assembly to the other part of the medicament delivery device; and (ii) the end user is not pressing on the delivery member to the distal direction (so the delivery member guard cannot move in to the proximal "free to move" position).

According to another embodiment, the body comprises a protrusion extending radially relative to the longitudinal axis, the delivery member guard comprises an arm with a distally directed surface facing a corresponding proximally directed surface of the protrusion of the body.

Preferably, according to another embodiment, the arm is flexible in the radial direction relative to the longitudinal axis, and the latch comprises a radially directed surface facing a corresponding radially directed surface on the arm of the delivery member guard.

According to another embodiment, when the lock member is in the locked position, the latch is restricted from moving in the proximal direction relative to the body.

Preferably, according to another embodiment, when the lock member is in the unlocked position, the latch is able to move in the proximal direction relative to the body, thereby providing space for the delivery member guard to travel in the distal direction by allowing the flexible arm to travel in the axial direction by moving axially past the radially directed surface of the latch and then moving radially past the protrusion of the body.

Preferably, according to another embodiment, the delivery member guard is partially arranged within the body.

Preferably, according to another embodiment, the delivery member guard partially surrounds the body.

Preferably, according to another embodiment, the latch is radially, relative to the longitudinal axis, arranged between the body and the delivery member guard, and the latch is axially movable relative to the delivery member guard in a proximal direction.

Preferably, according to another embodiment, the latch comprises a distally directed surface adjacent to a proximally directed surface of the delivery member guard.

Preferably, according to another embodiment, the device comprises a biasing member arranged between a distally directed surface of the delivery member guard and a proximally directed surface of the body.

Preferably, according to another embodiment, the distally directed surface of the arm of the delivery member guard is spaced apart from the proximally directed surface on the protrusion of the body when the delivery member guard is in the proximal position.

Preferably, according to another embodiment, the lock member is rotatable around the longitudinal axis relative to the body between the locked position and the unlocked position.

Alternatively, according to another embodiment, the lock member is removable relative to the body between the locked position and the unlocked position.

Preferably, according to another embodiment, the lock member is removable relative to the body, by being moved in a direction transverse to the longitudinal axis, between the locked position and the unlocked position.

Alternatively, according to another embodiment, the lock member is movable in a direction transverse to the longitudinal axis, between the locked position and the unlocked position.

Preferably, according to another embodiment, the lock member comprises a helical distally directed surface; and the distally directed surface of the lock member is a part of the helical distally directed surface.

Preferably, according to another embodiment, the helical distally directed surface comprises a distal end and a proximal end; and the distal end of the helical distally directed surface is adjacent to the proximally directed surface of the latch when the lock member is in the locked position.

Preferably, according to another embodiment, the proximally directed surface of the latch is configured to rotate, relative to the lock member, from the distal end of the helical distally directed surface towards proximal end of the helical distally directed surface when the lock member is rotated from the locked position to the unlocked position.

Preferably, according to another embodiment, the body comprises an inner body for accommodating a medicament container and an outer shell; at least a part of the delivery member guard and the latch are radially arranged between the inner body and the inner surface of the outer shell.

Preferably, according to another embodiment, the protrusion with the proximally directed surface protrudes from an outer surface of the inner body.

Preferably, according to another embodiment, the body comprises a bayonet connection on an outer surface of the body for attachment to a part of a medicament delivery device.

Preferably, according to another embodiment, the body comprises a snap-fit connection on an outer surface of the body for attachment to a part of a medicament delivery device.

Preferably, according to another embodiment, the lock member comprises a flange; the flange protrudes from the outer surface of the body; and the flange is aligned with the bayonet connection of the body in a longitudinal direction.

Preferably, according to another embodiment, the subassembly of this present disclosure can be used with a medicament delivery device cassette unit for a medicament delivery device; besides the medicament delivery device cassette unit, the medicament delivery device comprises a medicament delivery device drive unit, and the medicament delivery device cassette unit is releasably attached to the medicament delivery device drive unit.

Preferably, according to another embodiment, the medicament delivery device cis an injection device, an inhalation device or a medical sprayer.

Preferably, according to another embodiment, the medicament delivery device cassette unit is for accommodating a medicament container.

Preferably, according to another embodiment, the medicament delivery device drive unit comprises a driver for actuating the medicament contained in the medicament container accommodated by the medicament delivery device cassette unit.

Preferably, according to another embodiment, the sub-assembly comprises a distal lid attachable to the distal end of the body.

Preferably, according to another embodiment, the distal lid is a part of the body of the sub-assembly.

Preferably, according to another embodiment, the distal lid comprises a lid body formed in a shape in accordance with the shaped of the medicament container received within the body.

Preferably, according to another embodiment, the body comprises a tubular portion.

Preferably, according to another embodiment, the distal lid comprises a container support for supporting the medicament container received within the body; the container support comprises a proximally directed surface.

Preferably, according to another embodiment, the container support is a flexible arm.

Preferably, according to another embodiment, the flexible arm of the container support can be formed by a cut-out, opening towards the direction transverse to the longitudinal axis, on the lid body.

Preferably, according to another embodiment, the flexible arm may extend from the lid body towards the distal direction.

Preferably, according to another embodiment, the proximally directed surface of the container support is formed on an inner surface of the flexible arm or formed on a distal tip of the flexible arm.

Preferably, according to another embodiment, the container support is configured to prevent an axial movement of the medicament container received within the body in the distal direction and/or be used to tolerate the received medicament container with different dimension, e.g. certain length and/or width of the received medicament container, regarding to the engineering tolerance.

Preferably, according to another embodiment, the medicament delivery device with the sub-assembly as this present disclosure can be operated by a method comprising the step of connecting the cassette unit to the drive unit.

Preferably, according to another embodiment, the method comprises the step of connecting the cassette unit to the drive unit by rotating the cassette unit relative to the drive unit around the longitudinal axis.

Preferably, according to another embodiment, the method comprises the step of releasing the delivery member guard to move in a proximal direction relative to the medicament delivery device by rotating the lock member relative to the latch from locked position to the unlocked position;

Preferably, according to another embodiment, the method comprises the step of releasing the delivery member guard to move in a proximal direction relative to the medicament delivery device by rotating the locking member relative to the latch from locked position to the unlocked position.

Preferably, according to another embodiment, the method comprises the steps of releasing the delivery member guard to move in a distal direction relative to the medicament delivery device by a proximal movement of the delivery member guard; and triggering an operation of the medicament delivery device by distally moving the delivery member guard relative to the drive unit.

Preferably, according to another embodiment, the method comprises the steps of: connecting the cassette unit to the drive unit; releasing the delivery member guard to move in a proximal direction relative to the medicament delivery device by rotating the lock member relative to the latch from the locked position to the unlocked position; releasing the delivery member guard to move in a distal direction relative to the medicament delivery device by a proximal movement of the delivery member guard; triggering an operation of the medicament delivery device by distally moving the delivery member guard relative to the drive unit.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

Embodiments of the inventive concept will now be described, by way of example only, with reference to the accompanying drawings, in which.

DETAILED DESCRIPTION

Figure 1:
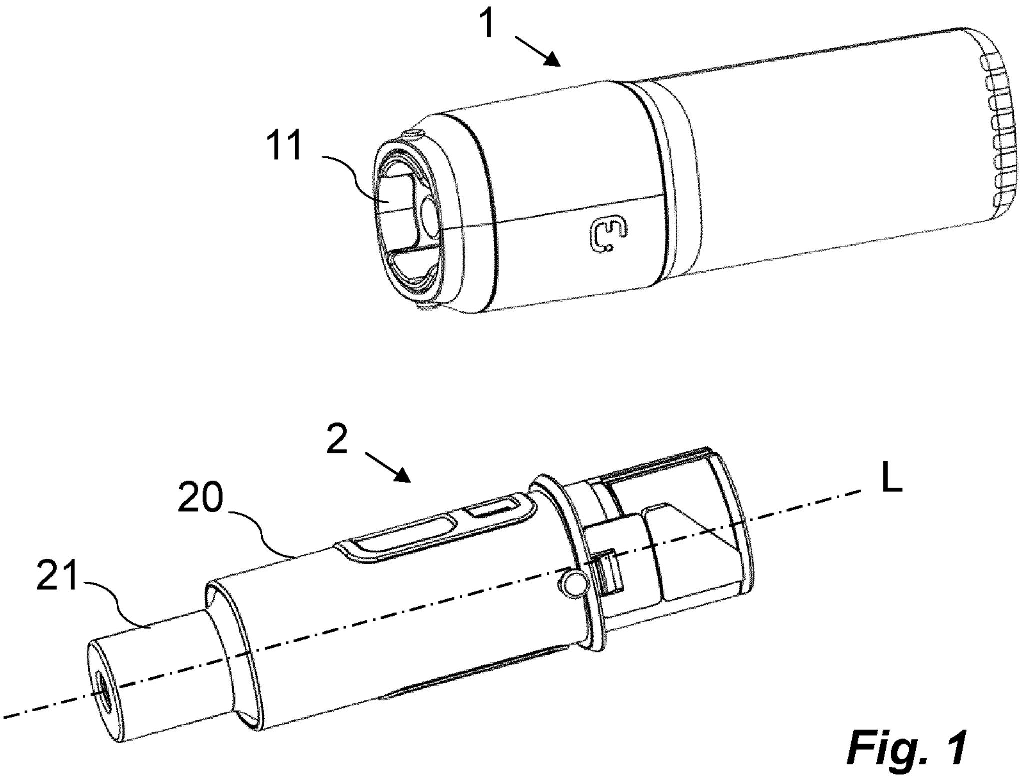
FIG. 1 schematically shows a perspective view of a medicament delivery device with a medicament delivery device cassette unit and a medicament delivery device drive unit.

FIGS. 1-12 illustrate a medicament delivery device with a medicament delivery device cassette unit. The medicament delivery device cassette unit is usually used with a medicament delivery device with two detachable parts, as shown in FIG. 1. The first part of the medicament delivery device, or the cassette 2, is usually for accommodating a medicament container 3, e.g. a syringe or cartridge, with a medicament contained within. The syringe or cartridge can be made of glass or plastic. The syringe or cartridge may comprise a rubber stopper sealing on a distal end of the syringe or cartridge, and a septum or delivery member with a rubber sheath sealing on a proximal end of the syringe or cartridge. Alternatively, the syringe or cartridge may be collapsible with only a septum or delivery member with a rubber delivery member sheath sealing on a proximal end of the syringe or cartridge.

The second part of the medicament delivery device, or a drive unit 1, is usually comprising a driver for actuating the medicament contained within the medicament container forward, expelled to an end user. The drive unit 1 may comprise a plunger rod for pushing on the medicament container. In one example, the stopper of the medicament container can be therefore moved in the proximal direction relative to the other part of the medicament container; In another example, the plunger rod may collapse the medicament container by pushing the medicament container in the proximal direction. The drive unit 1 also comprises a power source, such as a spring, a gas canister or a motor driven gear set, for forwarding the plunger rod. The focus of the concept described herein is a sub-assembly of the medicament delivery device cassette unit, not the drive unit, and various different types of drive unit could be used with the cassette units with the sub-assembly described herein. As such, the drive unit will not be comprehensively described.

The sub-assembly of the present disclosure comprises a body 20 extending along a longitudinal axis L from a proximal end to a distal end. In a preferred embodiment, the body 20 may be formed as a generally tubular shaped component, which is a shape similar to most common medicament containers, so that the device can be compact. However, the body can be formed in any other suitable shape that is able to contain the medicament container.

Figure 2:
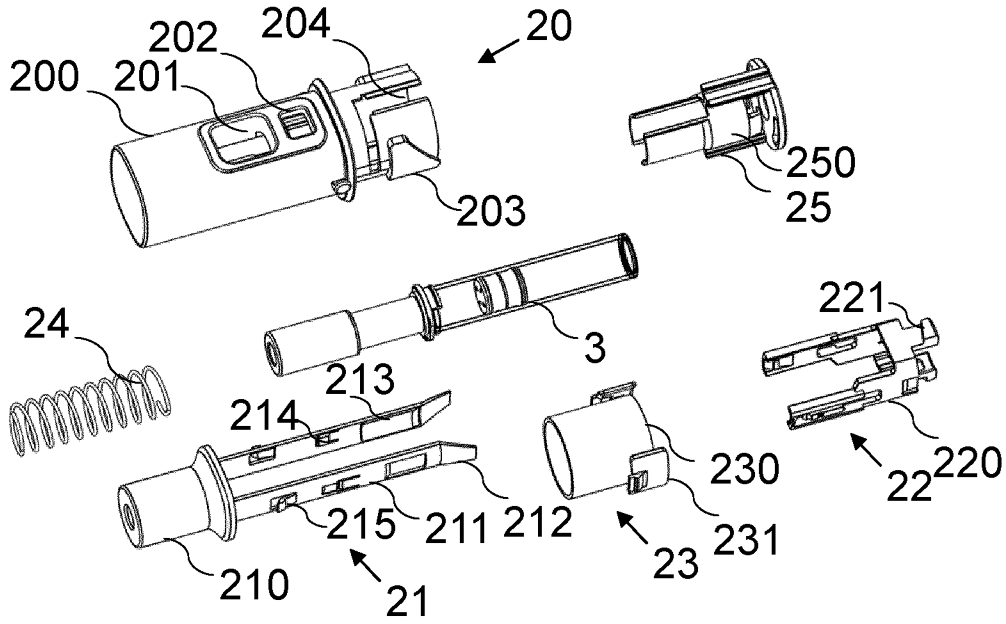
FIG. 2 schematically shows an exploded view of a sub-assembly of the medicament delivery device cassette unit of FIG. 1.
Figure 3:
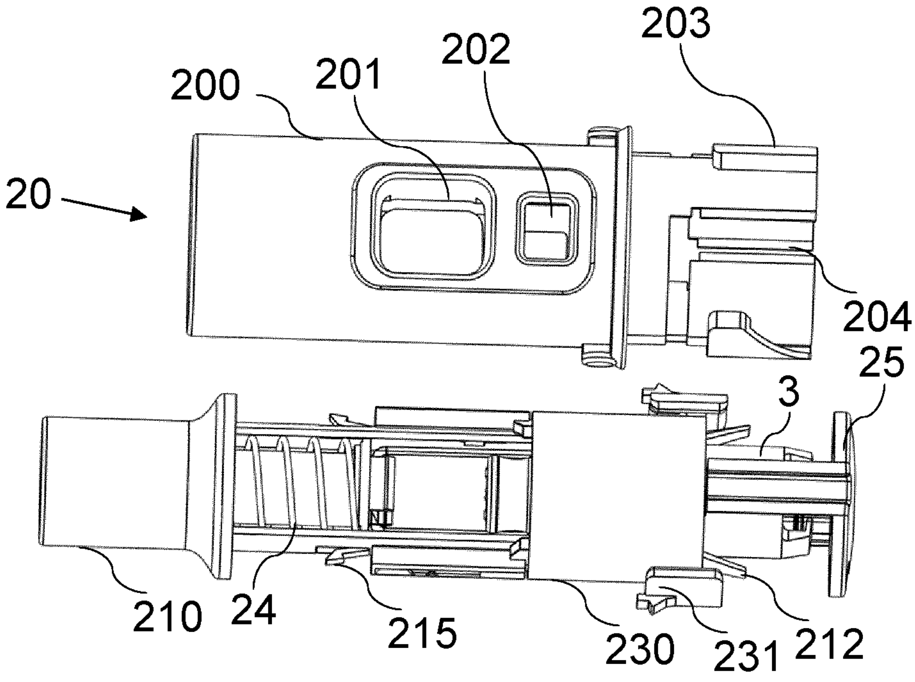
FIG. 3 schematically shows a perspective view of the sub-assembly of FIG. 2.
Figure 14:
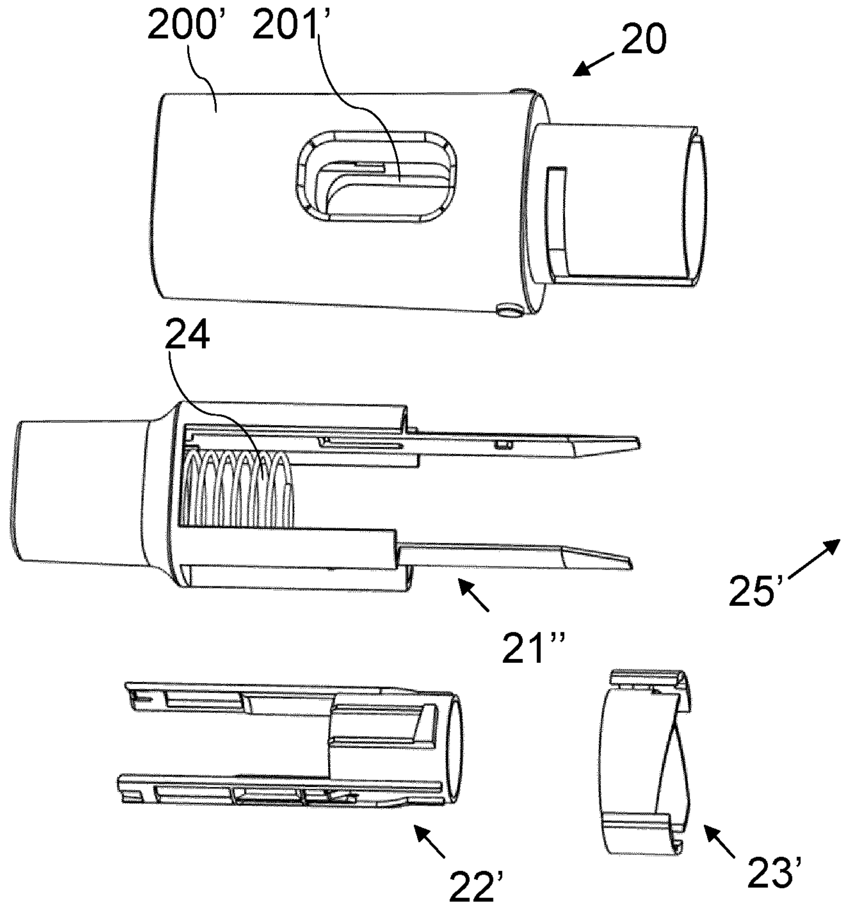

The body 20 is configured to accommodate the medicament container 3 in an outer shell 200. If visibility of the medicament container is required, the outer shell 200 may comprise a first window 201; 201' aligned with the medicament container 3, so that the end user can observe the medicament through the first window 201; 201', as shown in FIG. 2 and FIG. 14. On the other hand, the outer shell 200 may be transparent, so that the body does not need the first window. The outer shell 200 optionally comprises a second window 202, as shown in FIG. 2. The cassette unit 2 is configured to be releasably attached to the drive unit 1 through a releasable connection between the body 20 and the drive unit when the end user plans to carry out a medicament delivery operation. The body 20 comprises a connection configured to connect with a counter connection on the drive unit 1. In one example, the connection and the counter connection can form a bayonet connection, meaning that one of the body 20 and the drive unit 1 comprises a bayonet protrusion, and the other one of the body 20 and the drive unit 1 comprises a bayonet recess/cut-out. For example, the outer body 20 may comprise a bayonet connection 203 on the outer shell 200 of the body 20, such as a bayonet protrusion as shown in FIG. 2; and the drive unit 1 comprises a counter bayonet connection 11, such as a bayonet recess as shown in FIG. 1. In this example, the body 20 is configured to be axially inserted, along the L axis, into a proximal part of the drive unit 1, through the bayonet connection 203 and the counter bayonet connection 11; then the body 20 needs to be rotated relative to the drive unit 1, around the L axis, so that the cassette unit 2 is properly attached to the drive unit.

Alternatively, the connection between the body 20 and the drive unit 1 can be another suitable connection, such as a snap-fit connection or thread connection; or the cassette unit may be completely received into the drive unit; in this example, the portion of the drive unit for receiving the cassette unit may be a form-fit connection to releasably receive the cassette unit. In the case that the cassette unit is completely received into the drive unit, the shape of the body may be dependent on the shape of the portion of the drive unit for receiving the cassette unit.

The sub-assembly of the present disclosure comprises a delivery member guard 21, as shown in FIG. 2. The delivery member guard 21 comprises a front shield 210 configured to protrude from the proximal end of the body 20. The front shield 210 is configured to shield a medicament delivery member 31 integral with or being attachable to the medicament container 3 when the medicament delivery device is used by the end user. In a preferred example, the front shield 210 is a tubular shaped element with an opening in the proximal end of the front shield 210, so that the front shield 210 of the delivery member guard 21 can be coaxially attached to the body 20 and is axially movable relative to the body 20 along the longitudinal axis L between a distal position and a proximal position. Similarly, the front shield 210 of the delivery member guard is a similar shape to the body 20 to makes the device compact, but the delivery member guard can be also formed in any other suitable shape which can axially movable relative to the body 20 along the longitudinal axis L.

The delivery member guard 21 comprises an extension 211. The extension 211 extends axially from the front shield 210 toward the distal direction. In a preferred embodiment, the extension 211 is formed as a generally rectangular element with a length measured along the L axis being greater than a length measured in a direction transverse to the L axis; so that the cost of the delivery member guard 21 can be reduced (by reducing material). Alternatively, the extension 211 can be formed as the same shape as the shape of the front shield 210 of the delivery member guard 21, so that the manufacturing process can be simplified.

The extension 211 comprises an interaction part 212 on the distal end of the extension 211. The interaction part 212 is configured to interact with the drive unit 1 when the cassette unit 2 has been attached to the drive unit 1. The shape of the interaction part 212 may be dependent on the design of the drive unit 1.

For example, the drive unit 1 may comprise a motor, motor driven gear, a plunger rod and a mechanical switch for switching on the motor. The interaction part 212 of the delivery member guard 21 may be in contact with such mechanical switch and move the switch to switch on the motor when the delivery member guard 21 moves in the distal direction relative to the body 20 and the drive unit 1. In this case, if the switch is designed to face toward the proximal end of the drive unit 1 and the switch may be placed within a hole (for preventing any unintentional contact), the interaction part 212 may be a rod with a diameter that is able to insert into such hole and press on the switch. Alternatively, the switch may be laterally arranged on an inner surface of the drive unit 1. In this case, the interaction part 212 may be a radially outward protruding arm, so that the interaction part 212 can press on the switch or flip the switch over when the interaction part is aligned with the switch or moved past the switch.

In a preferred example, the extension also comprises a cut-out/recess 213. The cut-out/recess 213 defines a distal edge **213*a* (or will be also called a proximally directed surface 213*a*). The distal edge 213*a* is configured to interact with the latch 22** as will be explained later.

Figure 6:
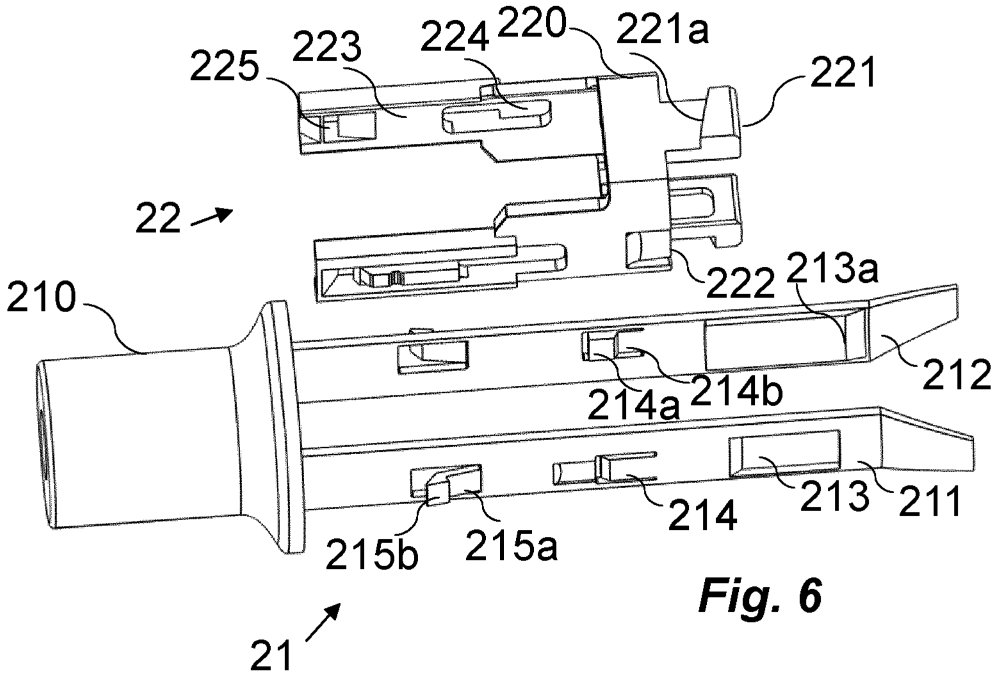
FIG. 6 schematically shows a perspective view of the delivery member guard and a latch of the sub-assembly of FIG. 2.

The delivery member guard 21 may comprise an arm 214. Preferably, the arm 214 is on the extension 211. The arm 214 can be formed by a longitudinal portion **214*b* longitudinally extending between a fixed end where the longitudinal portion 214*b* is fixed to the extension 211 of the delivery member guard 21, and a free end where the longitudinal portion 214***b* is not fixed to any part of the delivery member guard 21, as shown in FIG. 6. Alternatively, the arm 214 can be formed by a plurality of cut-outs or slots on the extension 211 of the delivery member guard 21, namely the arm can be formed as a radially flexible portion laterally arranged on the extension 211 of the delivery member guard 21.

The delivery member guard 21 may optionally comprise a locking tongue 215 on the extension 211, the locking tongue 215 radially flexes outward from the extension 211. The locking tongue 215 is configured to participate in an optional delivery member guard lock-out mechanism that will be explained later.

In a preferred example, the delivery member guard 21 is partially arranged within the body 20, namely the delivery member guard 21 is partially arranged within the outer shell 200 of the body 20. In this example, preferably, the extension 211 is fully arranged within the body 20; and the front shield 210 is fully or partially protruding from the proximal end of the body 20, so that the front shield 210 is able to cover the medicament delivery member 31.

Figure 10A:
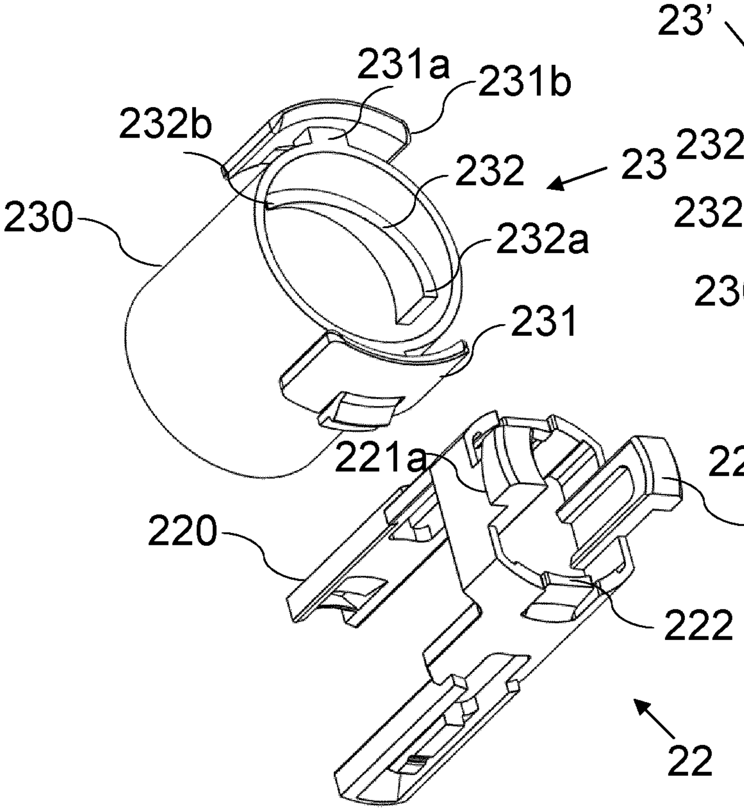
FIG. 10A schematically shows a perspective view of a lock member and the latch of the sub-assembly of FIG. 2.
Figure 10B:
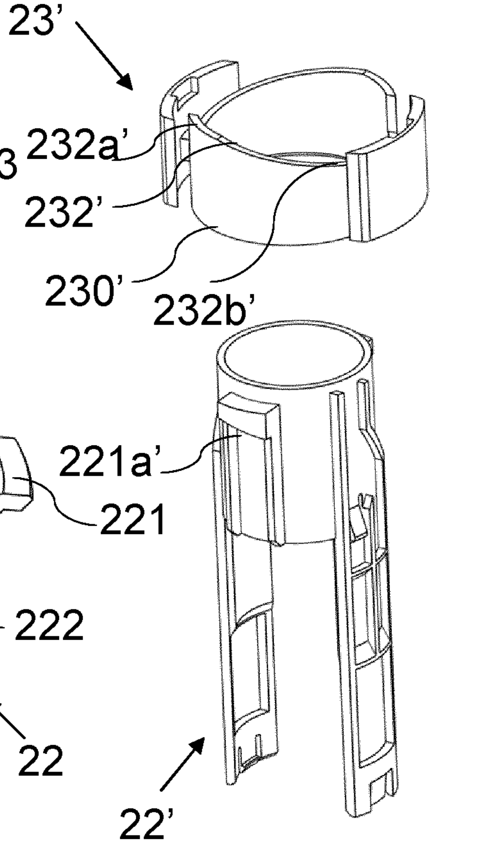

The device comprises a latch 22 attached to the delivery member guard 21, and a lock member 23 attached to the body 20, as shown in FIG. 2. The latch 22 comprises a latch body 220; the latch body 220 comprises a longitudinal part extending in a direction parallel to the longitudinal axis and a transverse part extending in a direction perpendicular to the longitudinal axis. The latch 22 comprises a distal extending arm 221 extending from the transverse part of the latch body 220 in the distal direction. The distal extending arm 221 comprises a protrusion protruding in the direction transverse to the longitudinal axis L. The protrusion comprises a proximally directed surface 221*a*; 221*a*'. as shown in FIG. 6 and FIGS. 10A-B. In a preferred example, the proximally directed surface 221*a*; 221*a*' is a ramp surface. In one example, the ramp surface in circumferentially inclined relative to the longitudinal axis L from one end to the other end; and in another example, the ramp surface inclines in a direction transverse to the longitudinal axis L from one end to the other end. The latch 22 comprises a distally directed surface 222 (shown in FIG. 6 and FIG. 10A). In a preferred example, the distally directed surface 222 is arranged on an edge of the transverse part of the latch body 220, as shown in FIG. 6. After assembly, the distally directed surface 222 is adjacent to the proximally directed surface 213*a* of the cut-out/recess 213 of the delivery member cover 21. The distal edge 213*a* of the cut-out/recess 213 of the delivery member cover 21 acts as a proximally directed surface 213*a*. The latch 22 is therefore attached to the delivery member guard 21 in the proximal direction, namely, the delivery member guard 21 cannot move relative to the latch 22 in the proximal direction, or in other words, the latch 22 cannot move relative to the delivery member guard 21 in the distal direction. However, the delivery member guard 21 is able to move relative to the latch 22 in the distal direction, or in other words, the latch 22 is able to move relative to the delivery member guard 21 in the proximal direction.

It should be noted that, alternatively, the proximally directed surface may be arranged on the latch body 220, so that the latch 22 does not need to comprise a distal extending arm 221. Further, the proximally directed surface 213*a* can be a radially extending arm extending from the extension 211 of the delivery member guard 21; so that the delivery member guard 21 may not comprise the cut-out/recess 213.

In a preferred example, the latch 22 is releasably attached to the delivery member guard 21. For example, the only connection for attaching the latch 22 to the delivery member guard 21 can be the proximally directed surface 213*a* and the distal direction surface 222, so that if the delivery member guard 21 moves in the distal direction relative to the latch 22, the latch 22 may no longer attach to the delivery member guard 21.

The latch 22 may comprise a blocking portion 223; preferably, the blocking portion 223 is arranged on the inner surface of the longitudinal part of the latch body 220, as shown in FIG. 6. The latch 22 may comprise a first a cut-out/recess 224, the latch optionally comprises a second cut-out/recess 225.

In a preferred embodiment, the latch 22 and the delivery member guard 21 are rotationally fixed to the body 20. The rotationally fixed arrangement can be achieved by, for example, a rib and slot connection between the latch 22 and the delivery member guard 21, and another rib and slot connection between the delivery member guard 21 and the body 20, e.g. the inner surface of the outer shell 200 and the outer surface of the extension 211. Alternatively, the rotationally fixed arrangement can be achieved by one or more axially extending protrusions on the inner surface of the body 20. The one or more axially extending protrusions are configured to align with the extension 211 of the delivery member guard 21 in the transverse direction. In this example, the latch 22 can be formed as a general rectangular shaped or square shaped element; so that the shape of the latch 22 can restrict a rotation of the latch 22 relative to the delivery member guard 21 and the body 20.

The sub-assembly of the present disclosure provides a lock mechanism to the latch 22 and the delivery member guard 21, and will now be explained.

The lock member 23 can be removably or irremovably attached to the body 20. The lock member 23 is movable relative to the body 20 in a locked position and an unlocked position. The lock member 23 comprises a distally directed surface adjacent to the proximally directed surface 221*a* of the latch 22 in the locked position; and the distally directed surface of the lock member 23 is spaced apart from the proximally directed surface 221*a* of the latch 22 in the unlocked position.

Figure 5A:
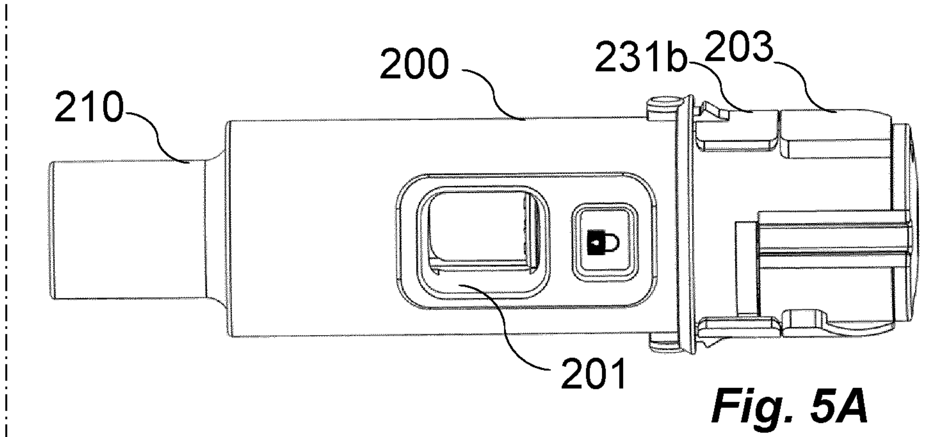
FIGS. 5A, 5B and 5C schematically show side views of the sub-assembly of FIG. 2 when a delivery member guard is in different positions.
Figure 5B:
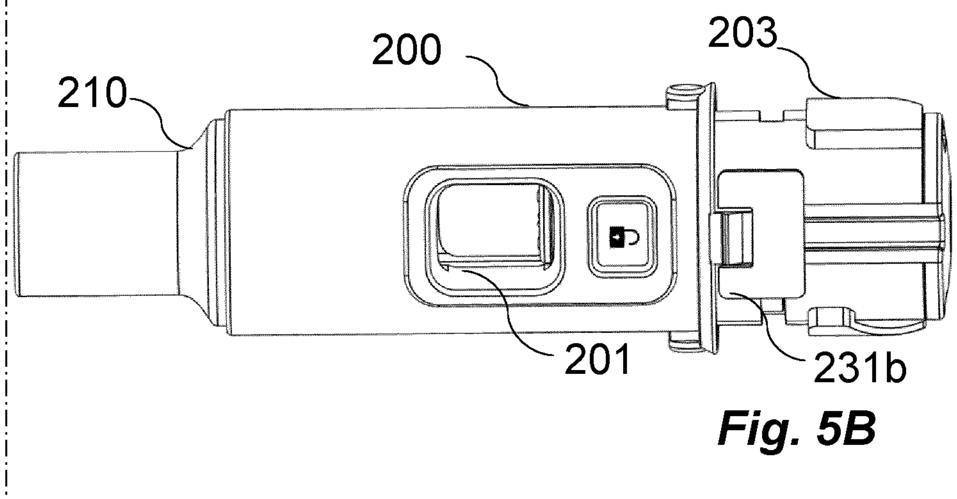

The device of the present disclosure is arranged so that when the lock member 23 is in the locked position, the delivery member guard 21 is locked in the distal position as shown in FIG. 5A; and when the lock member 23 is in the unlocked position, the delivery member guard 21 is released from the distal position; so that if the delivery member guard 21 is subjected to a proximal force, the delivery member guard 21 is able to move into the proximal position, as shown in FIG. 5B. This arrangement is achieved by attaching the latch 22 with the delivery member guard 21, at least in the proximal direction, and axially, releasably attach the latch 22 to the lock member 23, so that an engagement between the lock member 23 and the latch 22 can therefore keep the delivery member guard 21 in the distal position when the lock member 23 is in the locked position.

Figure 5C:
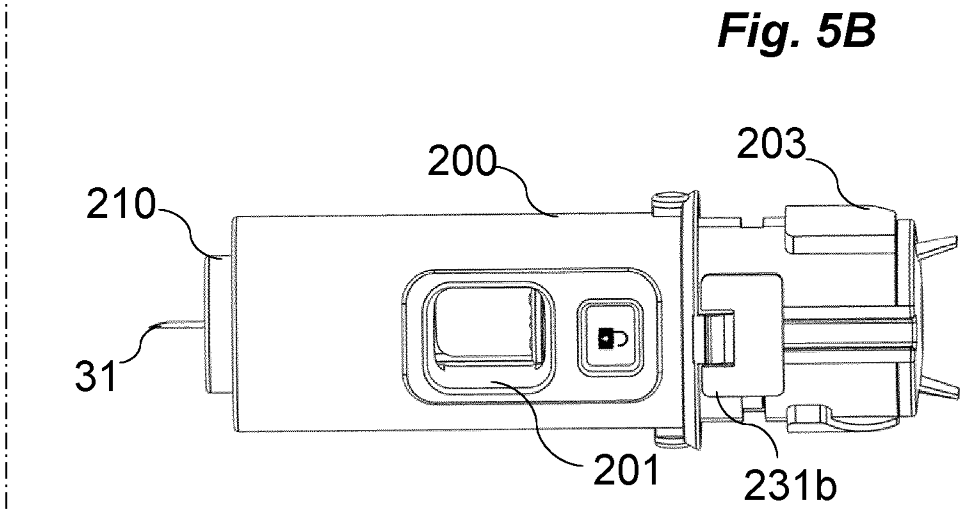

The movement of the delivery member guard 21 from the distal position to the proximal position can be used as an initiation of the cassette unit 2. For example, the delivery member guard 21 may be able to move into a further distal position (as shown in FIG. 5C) when the delivery member guard 21 has already moved into the proximal position from the distal position; further detail regarding this initiation mechanism will be explained later. Alternatively, the movement of the delivery member guard 21 from the distal position to the proximal position can be used in a cassette unit that the end user needs to self-attach to a medicament delivery member. For example, the end user may need to self-attach a pen needle to the cassette unit. In this example, the delivery member guard should be in the distal position at the beginning, so that the end user is able to attach the pen needle onto the cassette unit; when the end user attached the pen needle onto the cassette unit, the end user can move the lock member 23 from the locked position to the unlocked position, so that the delivery member guard 21 can move from the distal position to the proximal position, e.g. by simply being pulled by the user or pushed by a biasing member or resilient structure, so that the attached pen needle can be covered by the delivery member guard 21.

In one embodiment, the lock member 23 is removable relative to the body 20. The lock member can be a pin, a band or a strip, transversally movable relative to the body 20. The pin (or the band or the strip) comprises the distally directed surface adjacent to the proximally directed surface 221*a* of the latch 22 when the lock member is attached to the body 20, namely the lock member is in the locked position. When the lock member is detached from the body 20, namely when the lock member is in the unlocked position, the distally directed surface is spaced apart from the proximally directed surface 221*a* of the latch 22.

In another embodiment, the lock member 23 is irremovably attached to the body 20, and the lock member 23 is rotatable relative to the body 20 between the locked position and the unlocked position. In an example of this embodiment, the lock member 23 comprises a lock member body 230. The lock member body 230 may be a generally cylindrical shaped element or a generally hemicylindrical shaped element, for example. In a preferred example of this embodiment, the second window 202 of the body 20 is aligned with the lock member body 230. The lock member body 230 may comprise one or more indication marks, such as a text or symbol saying "locked", "unlocked"; or a circumferentially directed arrow. The one or more indication marks can be observed from the second window 202 when the cassette unit 2 is properly assembled, so that the end user can easily observe and identify whether the cassette unit 2 is locked or unlocked and ready for use.

Figure 15A:
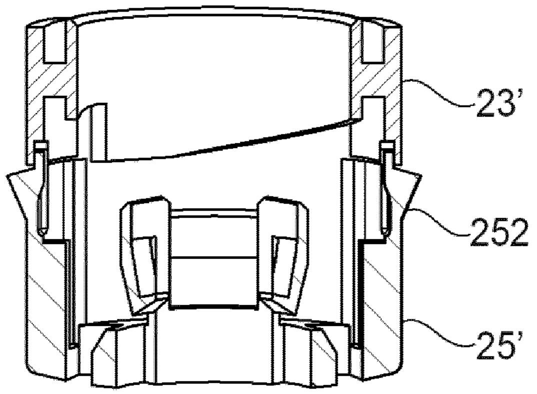
Figure 15B:
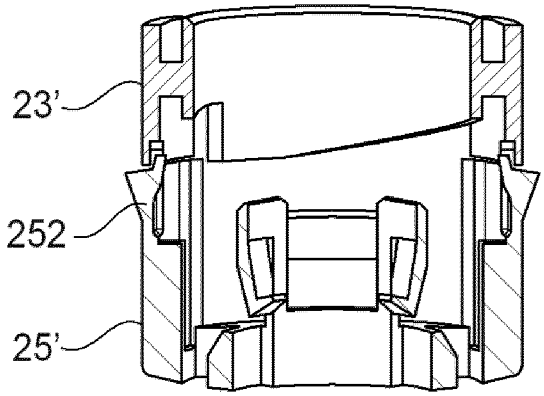

In another example, as shown in FIGS. 15A-B, an optionally lock member security mechanism can be provided. In an example, with a lock member 23' that is irremovably attached to the body 20; 20'. In this example, the distal lid 25' comprises a flexible tab 252 extending from a lid body 250 of the distal lid 25'. The flexible tab 252 comprises a protrusion protruding from a surface of the flexible tab 252. The lock member 23, in this example, comprises a recess/cut-out on the inner surface of the lock member body 230. When the flexible tab 252 is in a relaxed configuration, the protrusion is positioned within the recess/cut-out on the inner surface of the lock member body 230, therefore, the movement of the lock member 23' between the locked position and the unlocked position is prevented, as shown in FIG. 15A. The geometry of the protrusion of the flexible tab 252 and/or the recess/cut-out on the inner surface of the lock member body 230 is dependent on the movement of the lock member between the locked position and the unlocked position is prevented. For example, if the lock member is rotatable relative to the body 20, the recess/cut-out on the inner surface of the lock member body 230 may comprise two surfaces facing to the direction transverse to the longitudinal axis L. The rotation of the lock member relative to the body 20 between the locked position and the unlocked position can therefore be prevented. On the other hand, if the lock member is axially movable relative to the body 20, the recess/cut-out on the inner surface of the lock member body 230 may comprise a distally directed surface and a proximally directed surface. The axially movement of the lock member relative to the body 20 between the locked position and the unlocked position can therefore be prevented. The lock member security mechanism is configured to prevent the user accidentally move the lock member form the locked position and the unlocked position before the sub-assembly or cassette unit comprising the sub-assembly has been properly assembled (in manufacture stage) or properly attached to a part of a medicament delivery device. Therefore, the flexible tab 25 can be pressed into a tensioned configuration by a force applying on a surface of the flexible tab 25, preferably, the surface that is opposite to the surface that the protrusion is arranged on. For example, if the protrusion is arranged on the inner surface of the flexible tab, force should apply on the outer surface of the flexible tab, and vise versa.

When the flexible tab 25 is in the tensioned configuration, the protrusion moves out from the recess/cut-out on the inner surface of the lock member body 230, therefore, the lock member is free to move from the locked position and the unlocked position, as shown in FIG. 15B. The force for moving the flexible tab 25 to the tensioned configuration can be a force from an assembling tool used in the production line; or can be from a part of the medicament delivery device. For example, when the cassette unit comprising the sub-assembly attaches a front end of a drive unit of the medicament delivery device, an inner surface of a part of the drive unit may press the flexible tab to the tensioned configuration.

Figure 11:
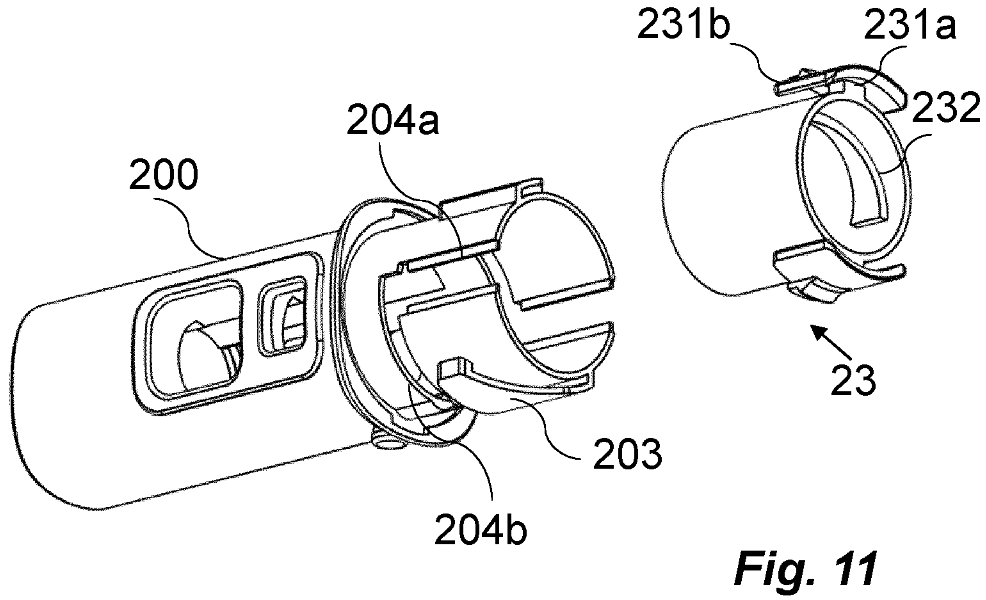
FIG. 11 schematically shows a perspective view of the lock member and the body of the sub-assembly of FIG. 2.

Further, the lock member 23 comprises a flange 231 as shown in FIG. 2. In this example, as shown in FIG. 11, the flange 231 comprises a transverse part 231*a* and an enlarged part 231*b*. The transverse part 231*a* extends between the enlarged part 231*b* and the lock member body 230. In this example, the body 20 comprises an assembly track 204 formed by a cut-out/recess, preferably on the distal end of the body 20, as shown in FIG. 11. The assembly track 204 comprises a longitudinal part 204*a* and a transverse part 204*b*. The longitudinal part 204*a* is a longitudinal cut-out/recess on the distal end of the body 20; and the transverse part 204*b* is a transverse cut-out/recess on the distal end of the body 20. The longitudinal part 204*a* of the assembly track 204 comprises a distal end and a proximal end. The transverse part 204*b* of the assembly track 204 comprises a first circumferential end and a second circumferential end. The proximal end of the longitudinal part 204*a* is connected to the first circumferential end of the transverse part 204*b* of the assembly track 204.

A dimension of the longitudinal part 204*a* and the transverse part 204*b*, observed from a direction transverse to the longitudinal axis L, is greater than a dimension of the transverse part 231*a* of the flange 231 of the lock member 23; but smaller than a dimension of the enlarged part 231*b* of the flange 231 of the lock member 23.

During assembly, the lock member 23 is configured to be attached to the body 20 through the flange 231 of the lock member 23 and the assembly track 204 of the body 20. The transverse part 231*a* of the flange 231 of the lock member 23 is aimed to the distal end of the longitudinal part 204*a* of the assembly track 204; inserted into the longitudinal part 204*a* through the distal end of the longitudinal part 204*a*; moved along the longitudinal part 204*a* of the assembly track 204 from the distal end of the longitudinal part 204*a* to the proximal end of the longitudinal part; entered into the transverse part 204*b* of the assembly track 204 from the first circumferential end of the transverse part 204*b*; and moved along the transverse part 204*b* of the assembly track 204 until being blocked by the second circumferential end of the transverse part 204*b*.

The dimension of the longitudinal part 204*a* and the transverse part 204*b* is smaller than a dimension of the enlarged part 231*b* of the flange 231 of the lock member 23, so a transverse movement of the lock member 23 relative to the body 20 is blocked by the enlarged part 231*b*.

In one preferred embodiment, the latch 22 and the delivery member guard 21 are rotationally attached to the body 20, by an arrangement as mentioned above. In one example of this embodiment, the enlarged part 231*b* of the flange 23 protrudes from the outer surface of the distal end of the outer shell 200 of the body 20. In a preferred example, the bayonet connection 203 of the body 20 is a bayonet protrusion. The flange 23, specifically the enlarged part 231*b* of the flange 23 is aligned with the bayonet connection 203 of the body 20 in a longitudinal direction, as shown in FIG. 5A. The enlarged part 231*b* of the flange 23 may have a circumferential length that is generally equal to or slightly smaller than a circumferential length of the bayonet connection 203; so that when the bayonet protrusion 203 moves in a longitudinal portion of the counter bayonet connection 11, the enlarged part 231*b* of the flange 23 can also move into the longitudinal portion of the counter bayonet connection 11. However, when the bayonet protrusion 203 moves into a circumferential portion of the counter bayonet connection 11, the enlarged part 231*b* of the flange 23 can only stay in the longitudinal portion of the counter bayonet connection 11; so that when the bayonet protrusion 203 rotates along the circumferential portion of the counter bayonet connection 11, the body 20, the delivery member guard 21 and the latch 22 are all rotated relative to the lock member 23. The rotation for connecting the cassette unit 2 to the drive unit 1 therefore causes the lock member 23 to rotate relative to the latch 22 from the locked position to the unlocked position.

Figure 12:
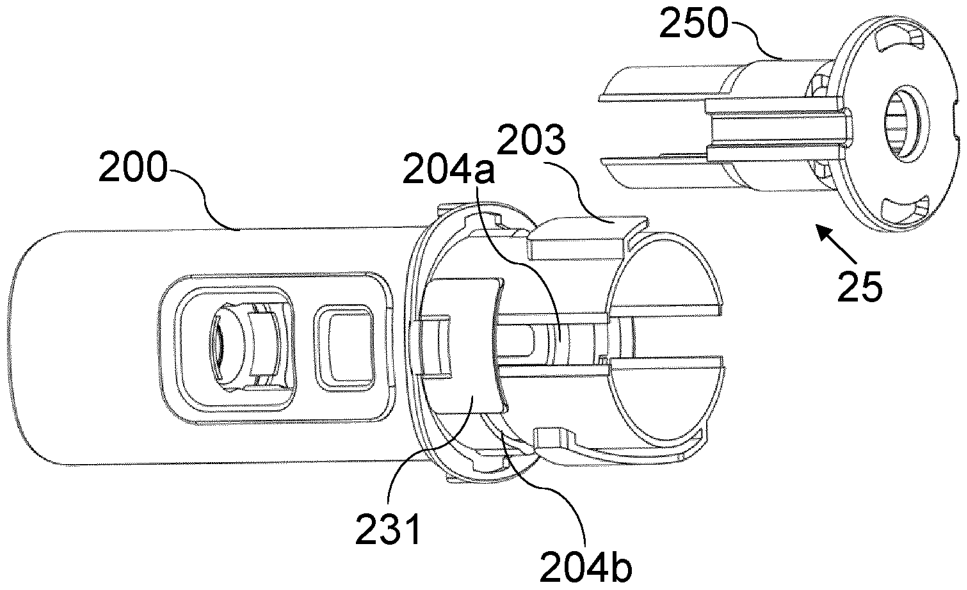
FIG. 12 schematically shows a perspective view of a distal lid and the body of the sub-assembly of FIG. 2.

In a preferred example of this embodiment, the device comprises a distal lid 25; 25', as shown in FIG. 2 and FIG. 12. The distal lid 25; 25' is configured to attach to the distal end of the body 20, so that a movement of the medicament container 3 in the distal direction can be blocked. The distal lid 25; 25' can also be fully or at least partially received within the longitudinal part 204*a* of the assembly track 204, so that the lock member 23 can only be rotatable relative to the body 20 along the transverse part 204*b* of the assembly track 204.

The shape of the distal lid 25; 25' is typically dependent on the shape of the distal end of the body 20. The distal lid 25; 25' typically comprises an opening axially aligned with a portion of the distal end of the medicament container 3, so that when the cassette unit 2 is attached to the drive unit 1, the plunger rod is able to pass through the opening and act on the medicament container 3 for delivering the contained medicament.

Figure 7:
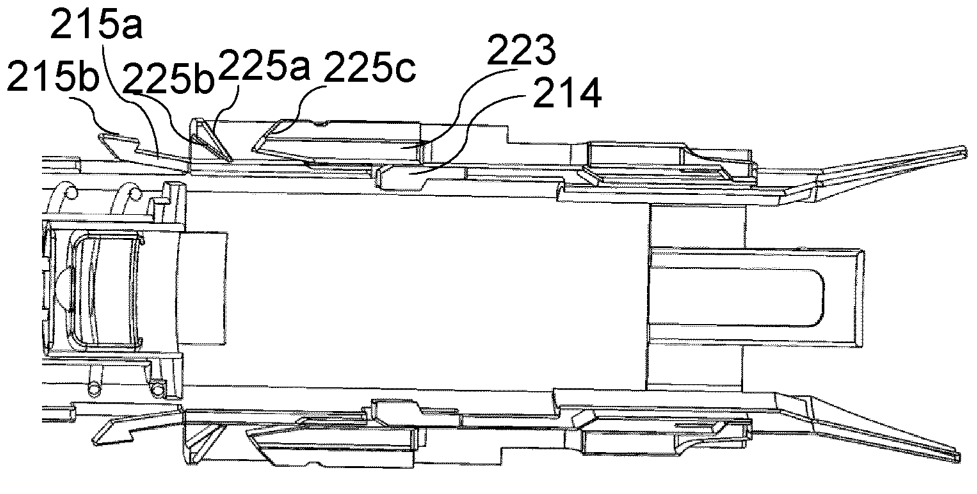
FIG. 7 schematically shows a cross-section view of the delivery member guard, a biasing member and the latch of the sub-assembly of FIG. 2.

The distal lid 25; 25' comprises the lid body 250, as shown in FIG. 2 and FIG. 7; the lid body 250 can be formed in accordance with the shaped of the medicament container received within the body 20, for example, the lid body 250 comprises a tubular portion.

In one example, the distal lid 25; 25' may comprise a curve shaped opening/slot (when observed from the axial direction), so that the interaction part 212 of the delivery member guard 21 can pass through the curve shaped opening/slot and protrude into the drive unit 1. In another example, the distal lid 25; 25' may be a generally rectangular or oval shaped element. In this example, the interaction part 212 of the delivery member guard 21 can pass through from a space between the distal edge of the body 20 and an edge of the back lid 25.

The distal lid 25; 25' optionally comprises a label, e.g. RFID tag, bar code, QR code or mechanical code, for containing information about the cassette unit 2 or the contained medicament, so that a reader in the drive unit 1 may get the information for a further use, dependent on the design.

The distal lid 25; 25' optionally comprises a container support 251 for supporting the medicament container received within the body 20. In one example, the container support 251 is a flexible arm 251. The flexible arm 251 can be formed by a cut-out, opening towards the direction transverse to the longitudinal axis L, on the lid body 250; alternatively, the flexible arm 251 may extend from the lid body 250 towards the distal direction. The proximally directed surface of the container support 251 can be formed on an inner surface of the flexible arm; or can be formed on a distal tip of the flexible arm. In this example the container support 251 can prevent an axial movement of the medicament container received within the body 2 in the distal direction. The container support 251 may also be used to tolerate the received medicament container with different dimension, e.g. certain length and/or width of the received medicament container, regarding to the engineering tolerance.

In an example of the embodiment, the lock member 23 comprises a protrusion. The protrusion protrudes from an inner surface of the lock member body 230.

In one example, the protrusion comprises the distally directed surface of the lock member. When the lock member is in the locked position, the distally directed surface of the lock member is adjacent to the proximally directed surface of the latch. When the lock member is rotated relative to the body to the unlocked position, the distally directed surface of the lock member is axially offset relative to the proximally directed surface of the latch, so that the distally directed surface of the lock member is spaced apart from the proximally directed surface of the latch.

In another example, the protrusion comprises a helical distally directed surface 232. Alternatively, in another example, instead of the protrusion of the lock member, the lock member body 230' may comprises a helical distally directed surface 232' on a distal end of the lock member body 230', as shown in FIG. 10B. The distally directed surface of the lock member 23 is a part of the helical distally directed surface 232. The helical distally directed surface circumferentially inclines, relative to the lock member body 230, from a proximal end 232*b* to a distal end 232*a*. The helical distally directed surface may be a generally curved surface or a straight surface; furthermore, the helical distally directed surface may be a generally smooth surface or the helical distally directed surface may comprise a plurality of protrusions between the distal end 231*a* and the proximal end 231*b*, so that the end user may have some tactile feedback when manipulating the sub-assembly of the present disclosure.

The helical distally directed surface 232 is configured to provide a lock reverse mechanism to the end user, namely, the end user moves the lock member 23 from the locked position to the unlocked position, the end user is able to move the lock member 23 from the unlocked position back to the locked position; meanwhile the lock mechanism to the latch 22 and the delivery member guard 21 can be also reversed back to an initial locked position.

The helical distally directed surface 232 is an optional feature for the lock mechanism to the latch 22 and the delivery member guard 21, namely, whether the lock member 23 comprises a helical distally directed surface 232 or not will not bring any impact to the lock mechanism to the latch 22 and the delivery member guard 21; as mentioned above, the distally directed surface of the lock member doesn't need to be formed as a helical surface (namely extending in the circumferential and longitudinal direction).

The distal end 232*a*, which also acts as the distally directed surface, of the helical distally directed surface 232 is adjacent to the proximally directed surface 221*a* of the latch 22, when the lock member 23 is in the locked position; when the lock device is rotated relative to the longitudinal axis L from the locked position to the unlocked position, the proximal directed surface 221*a* of the latch 22 is rotated, relative to the lock device body 230, from the distal end 232*a* of the helical distally directed surface 232 towards the proximal end 232*b* of the helical distally directed surface 232. In a preferred embodiment, the proximal directed surface 221*a* of the latch 22 is adjacent to the proximally directed surface 221*a* of the latch 22, when the delivery member guard 21 is subjected to the proximal force, and when the lock member 23 is in the unlocked position. In another example, the proximal directed surface 221*a* of the latch 22 can move along the helical distally directed surface 232 from the distal end 232*a* of the helical distally directed surface 232 to the proximal end 232*b* of the helical distally directed surface 232 when the lock member 23 is rotated from the locked position to the unlocked position, if the delivery member guard 21 is continuously subjected to the proximal force. In this example, an axial length measured from the distal end 232*a* of the helical distally directed surface to the proximal end 232*b* of the helical distally directed surface should be equal or greater than the moving distance of the delivery member guard 21 when it moves from the distal position to the proximal position. In this example, the proximally directed surface 221*a* of the latch 22 travels along the helical distally directed surface 232 from the distal end 232*a* to the proximal end 232*b*, so that if the lock member 23 is rotated relative to the body 20 from the unlocked position to the locked position, the proximally directed surface 221*a* of the latch 22 will again travel along the helical distally directed surface 232 from the proximal end 232*b* to the distal end 232*a* (namely, the distally directed surface). When the proximally directed surface 221*a* of the latch 22 meets the distal end 232*a* (namely, the distally directed surface), the delivery member guard 21 will be also lifted back to the distal position from the proximal position by the latch 22, due to the engagement between the distally directed surface 222 of the latch 22 and the proximally directed surface 213*a* of the delivery member guard 21.

For providing the proximal force that is configured to move the delivery member guard 21 from the distal position to the proximal position, the device can optionally comprise a biasing element 24, preferably arranged between a distally directed surface of the delivery member guard and a proximally directed support surface of the body. The biasing element 24 is configured to provide the proximal force to the delivery member guard 21. Alternatively, the delivery member guard 21 may comprise a resilient arm arranged on the distal end of the delivery member guard radially protruding from the delivery member guard; so that an axial compression of the resilient arm can provide the proximal force to the delivery member guard.

As mentioned above, the movement of the delivery member guard 21 from the distal position to the proximal position can make the cassette unit 2 ready for use. For example, the delivery member guard 21 may be able to move from the distal position into a more distal position (as shown in FIG. 5C) after the delivery member guard 21 has already moved into the proximal position from the distal position.

In one example of the initiation mechanism, the latch 22 is only engaged with the delivery member guard 21 in the proximal direction; namely, the delivery member guard 21 cannot move relative to the latch 22 in the proximal direction, or in other words, the latch 22 cannot move relative to the delivery member guard 21 in the distal direction. However, the delivery member guard 21 is able to move relative to the latch 22 in the distal direction, or in other words, the latch 22 is able to move relative to the delivery member guard 21 in the proximal direction.

The delivery member guard 21 comprises the arm 214. As mentioned above, preferably the arm 214 is on the extension 211 of the delivery member guard 21. The arm 214 comprises a protrusion 214*a*. In a preferred example, the protrusion 214*a* of the arm 214 radially extends from the radially flexible portion toward the longitudinal axis L. The protrusion 214*a* comprises a distally directed surface.

The latch 22 comprises the blocking portion 223, as mentioned above. Preferably, the blocking portion 223 is arranged on the inner surface of the longitudinal part of the latch body 220, as shown in FIG. 6. In a preferred example, the latch 22 comprises a first a cut-out/recess 224.

The blocking portion 223 of the latch 22 is configured to align with the arm 214 of the delivery member guard 21 in the transverse direction relative to the longitudinal axis.

Figure 4:
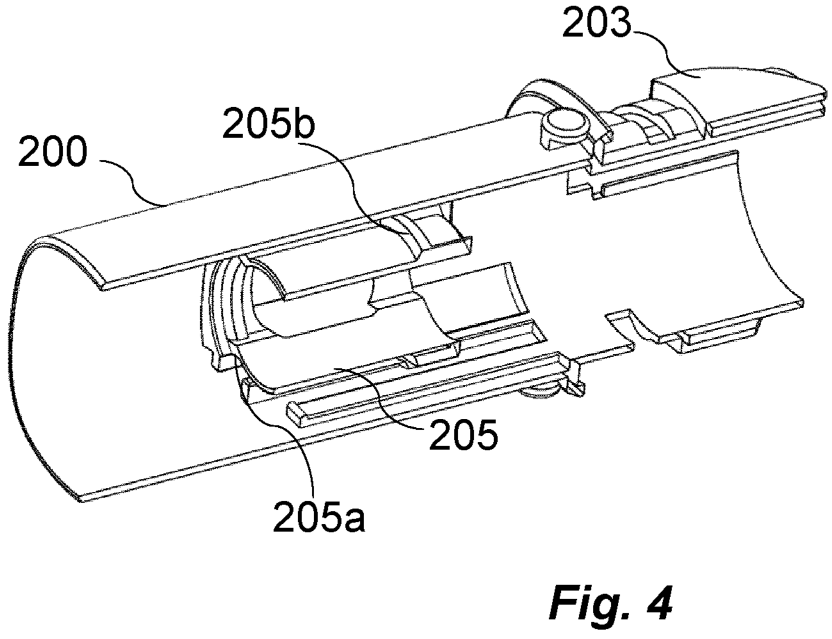
FIG. 4 schematically shows a cross-section perspective view of a body of the sub-assembly of FIG. 2.

In a preferred example, the body 20 comprises an inner body 205 for accommodating a medicament container 3, as shown in FIG. 4. In a preferred example, at least a part of the delivery member guard 21 and the latch 22 are radially arranged between the inner body 205 and the inner surface of the outer shell.

The shape of the inner body 205 is dependent on the shape of the inner surface of the body 20 and on the shape of the medicament container 3. The inner body 205 is fixed to the inner surface of the body 20. A dimension of the inner body 205 should be smaller than a dimension defined by the body 20, so that a space can be defined between the inner body 205 and the inner surface of the body 20. The space is configured to receive the extension 211 of the delivery member guard 21, so that the delivery member guard 21 is able to move axially relative to the body 20 and the inner body 205.

Figure 8A:
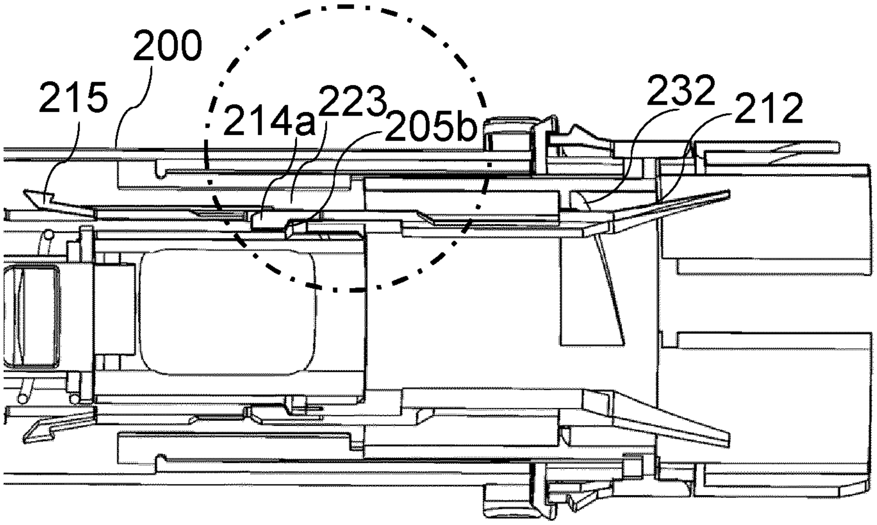
FIGS. 8A-8B schematically shows a cross-section view of the device of FIG. 2 in a locked position.
Figure 8B:
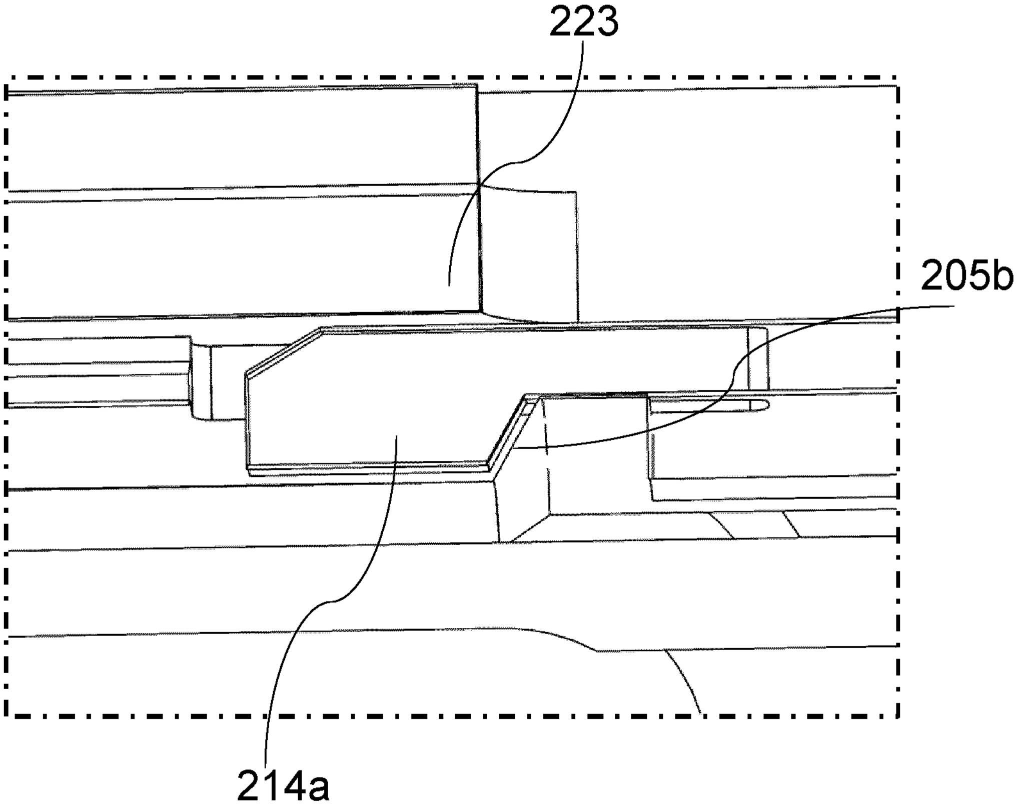

In this example, the inner body 205 comprises a protrusion that protrudes from an outer surface of the inner body 205 towards the inner surface of the body 20. The protrusion 205*b* comprises a proximally directed surface. When the delivery member guard 21 is in the distal position, the distally directed surface on the protrusion 214*a* of the delivery member guard 21 is adjacent to the proximally directed surface on the protrusion 205*b* of the inner body 205, as shown in FIG. 8A. FIG. 8B illustrates only the part of FIG. 8A that is highlighted with a dashed line. When the delivery member guard 21 is in the distal position, the distally directed surface is adjacent to the proximally directed surface, so that the delivery member guard 21 cannot move relative to the body 20 in the distal direction.

Figure 9A:
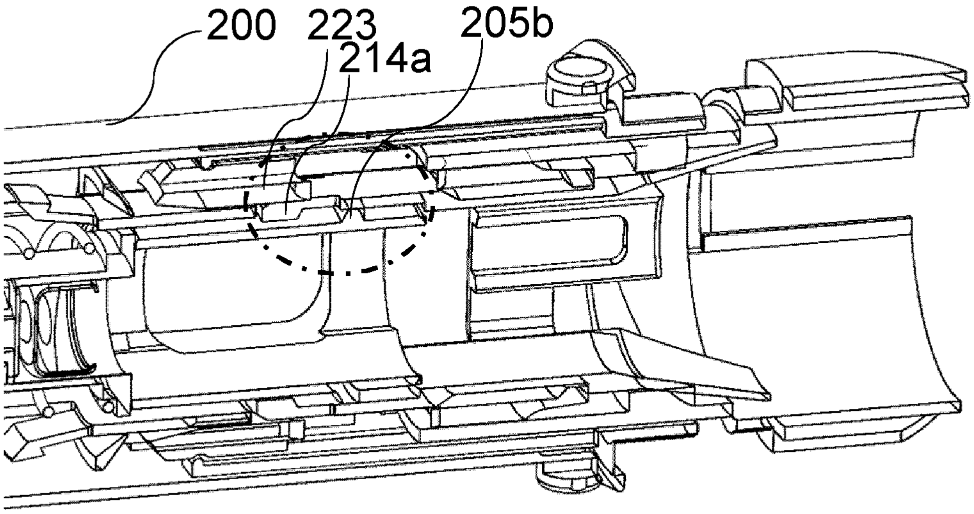
FIGS. 9A-9B schematically shows a cross-section view of the device of FIG. 2. in an unlocked position.
Figure 9B:
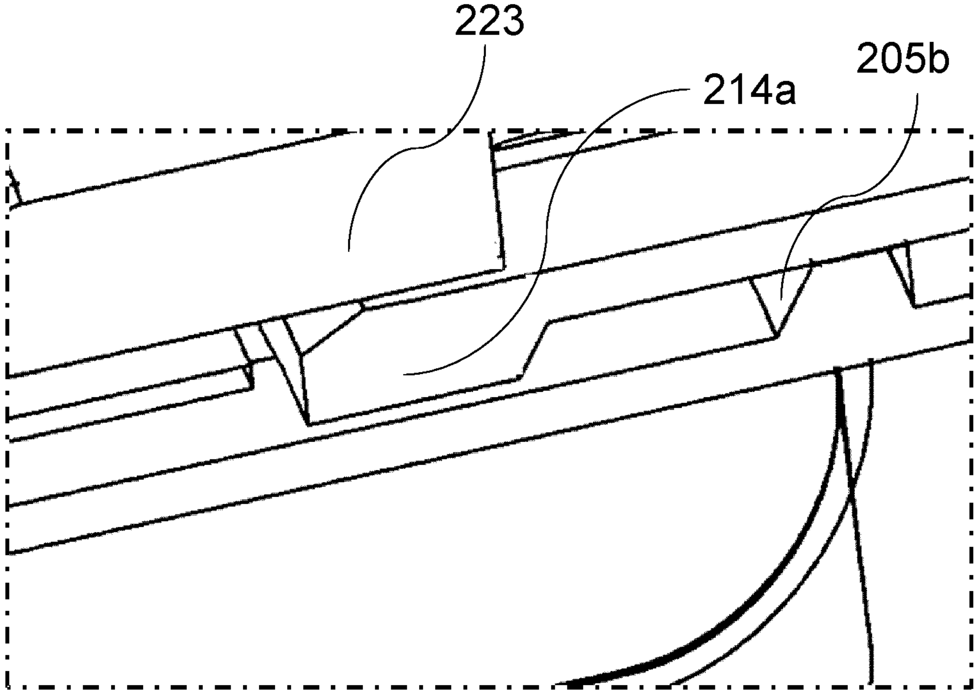

When the lock member 23 is in the unlocked position, the delivery member guard 21 is able to move into the proximal position, and when the delivery member guard is in the proximal position, as shown in FIG. 9A. FIG. 9B illustrates the part of FIG. 9A that is highlighted with a dashed line. The distally directed surface on the protrusion 214*a* of the delivery member guard 21 is spaced apart from the proximally directed surface on the protrusion 205*b* of the inner body 205. Once the distally directed surface of the delivery member guard 21 is spaced apart from the proximally directed surface of the inner body 205, the delivery member guard 21 is able to move relative to the body 20 in the distal direction.

When the delivery member guard 21 is in the proximal position, the distal movement of the delivery member guard 21 relative to the body 20 causes the delivery member guard 21 to move in the distal direction relative to the latch 22. The movement of the delivery guard 21 relative to the latch 22 causes the arm 214 of the delivery member guard 21 to move to align with the cut-out/recess 224 of the latch 22 in the transverse direction. A further movement of the delivery member guard 21 in the distal direction relative to the body 20 causes the distally directed surface on the protrusion 214*a* of the delivery member guard 21 to contact the proximally directed surface on the protrusion 205*b* of the inner body 205—since the arm 214 of the delivery member guard 21 is aligned with the cut-out/recess 224 of the latch 22 in the transverse direction, the arm 214 of the delivery member guard 21 will flex outward when the distally directed surface on the protrusion 214*a* of the delivery member guard 21 contacts the proximally directed surface on the protrusion 205*b* of the inner body 205. Once the arm 214 of the delivery member guard 21 flexes outward, the protrusion 214*a* of the delivery member guard 21 is able to pass the protrusion 205*b* on the inner body 205, so that any further distal movement of the delivery member guard 21 is not blocked by the inner body 205 anymore.

In one embodiment, the inner body 205 is configured to accommodate the medicament container 3. In this embodiment, the inner body 205 comprises a window transversally aligned with the first window 201; 201' on the body 20. Preferably, the inner body 205 is a generally cylindrical shaped element and defines an interior cavity. The medicament container 3 is configured to be at least partially received within the interior cavity of the inner body 205. The inner body may comprise a support 205*a* adjacent to a front neck portion or a rear flange portion of the medicament container 3. For example, the support 205*a* may be a plurality of inwardly directed protrusions arranged on the proximal end of the inner body 205, as shown in FIG. 4. The plurality of inwardly directed protrusions is configured to engage with the front neck portion of the medicament container 3. Alternatively, the support may be arranged on the distal end of the inner body 205, so that the support can engage with the rear flange of the medicament container 3. The support can be generally rigid or resilient. The support can be an integral part of the inner body 205, as shown in FIG. 4, or can be an independent component, e.g. a cushion or washer, attached to the inner body 205.

It should be noted that the body 20 may alternatively comprise a hook on the inner surface as the protrusion with the proximally directed surface. Further, the inner body 205 can be integral to the body 20 or can be an independent component attached to the body 20.

The sub-assembly of the present disclosure can be operated by the end user with the steps of: attaching the cassette unit 2 to the drive unit 1, preferably through the bayonet connection between the cassette unit 2 and the drive unit; releasing the delivery member guard 21 to move in a proximal direction relative to the medicament delivery device by moving the lock member 23 relative to the latch 22 from locked position to the unlocked position, preferably, by rotating the lock member 23 relative to the latch 22 while the end user rotates the cassette unit 2 to the drive unit 1 for connecting the cassette unit 2 to the drive unit 1 through the bayonet connection. The operation method further comprises the steps of releasing the delivery member guard 21 to move in the distal direction relative to the medicament delivery device by the proximal movement of the delivery member guard 21; and triggering an operation of the medicament delivery device by distally moving the delivery member guard 21 relative to the drive unit 1.

The sub-assembly of the present disclosure may comprise a delivery member guard lock-out mechanism. In one example of the delivery member guard lock-out mechanism, the delivery member guard 21 comprises the locking tongue 215 on the extension 211, and the locking tongue 215 radially flexes outward from the extension 211. The locking tongue 215 comprises an arm 215*a* extending from the extension 211 of the delivery member guard 21 towards the proximal direction of the delivery member guard 21, as shown in FIG. 6. The locking tongue 215 comprises a protrusion 215*b* on a proximal tip of the arm 215*a* of the locking tongue 215. In this example, the latch 22 comprises the second cut-out/recess 225. The cut-out/recess 225 comprises a first proximally directed surface 225*a*, a second proximally directed ramp surface 225*b* and a third distally directed surface 225*c*.

In this example, the device comprises an optional biasing member 24 arranged between the third distally directed surface of the delivery member guard 21 and the third proximally directed surface of the body 20 for biasing the delivery member guard 21 in the proximal direction. Alternatively, the delivery member guard 21 may comprise a resilient arm for biasing the delivery member guard 21 in the proximal direction.

As shown in FIG. 7, when the delivery member guard 21 is in the distal position, the locking tongue 215 is closer to the proximal end of the body 20 than the second cut-out/recess 225. When the delivery member guard 21 moves into the proximal position, then moves to the further distal position, for revealing the medicament delivery member 31 to perform the medicament delivery operation, the locking tongue 215 will move past the cut-out/recess 225 in the distal direction.

When the second proximally directed ramp surface 225*b* is configured to engage with the protrusion 215*b* when the locking tongue 215 move past the cut-out/recess 225. The engagement between the second proximally directed ramp surface 225*b* and the protrusion 215*b* of the locking tongue 215 causes the locking tongue 215 to flex radially inward, so that the protrusion 215*b* of the locking tongue 215 does not get stuck in the cut-out/recess 225.

When the delivery operation is finished, the end user may lift the cassette unit 2 from the medicament delivery site. The delivery member guard 21 is biased to the proximal direction. When the locking tongue 215 moves and aligns with the cut-out/recess 225, the locking tongue 215 will flex outward; and the protrusion 215*b* on the locking tongue 215 will move into the cut-out/recess 225.

Figure 13:
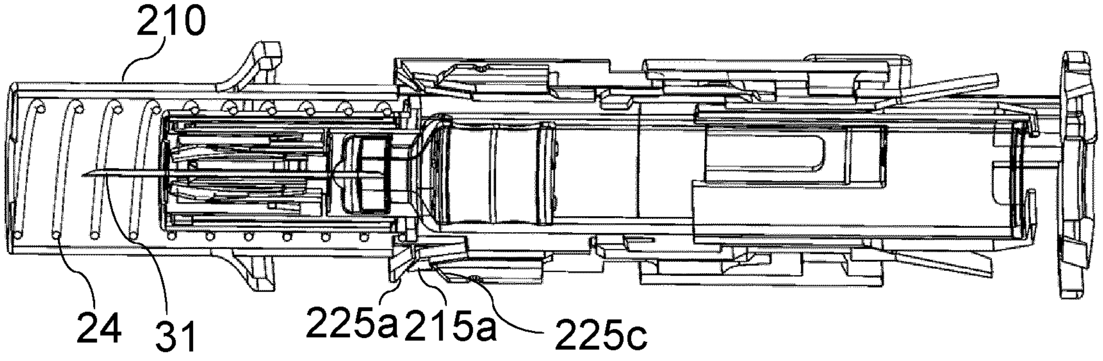
FIG. 13 schematically shows a cross-section view of the sub-assembly of FIG. 2 when the delivery member guard is in a lock-out position.

When the protrusion 215*b* on the locking tongue 215 moves into the cut-out/recess 225, the protrusion 215*b* on the locking tongue 215 will be blocked by the first proximally directed surface 225*a* and the third distally directed surface 225*c*, in both the distal direction and the proximal direction as shown in FIG. 13.

Figure 16:
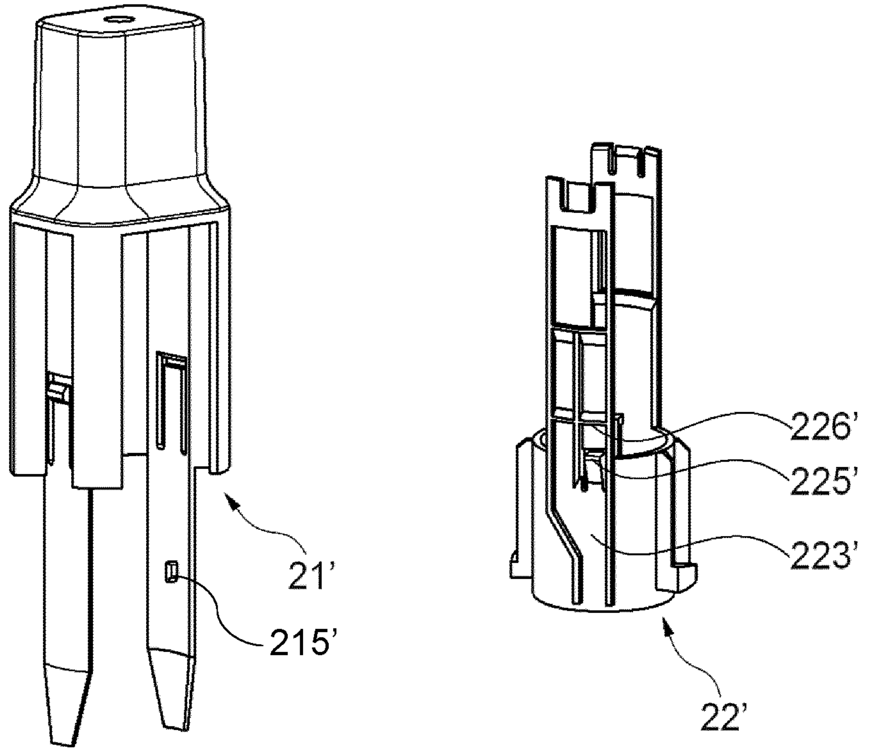
Figure 17A:
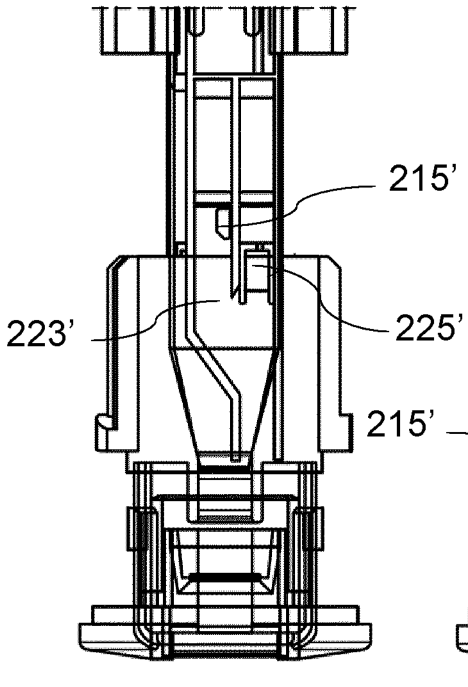
Figure 17B:
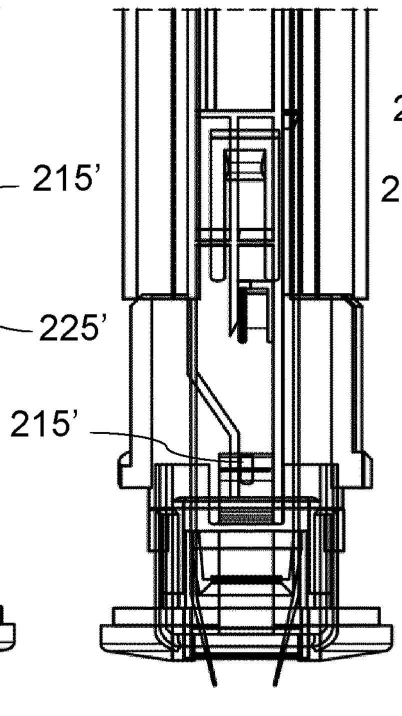
Figure 17C:
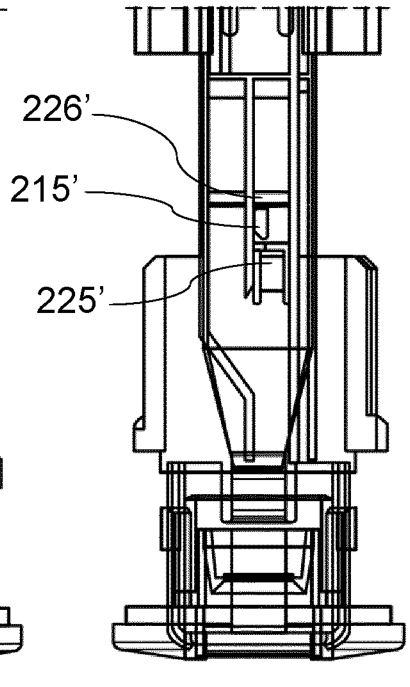

Another example of the delivery member guard lock-out mechanism as shown in FIGS. 16-17C. In this example, the latch 22' and the delivery member guard 21' are rotatable or linearly movable, in the direction transverse to the longitudinal axis L, related to each other after the lock member 23; 23' is in the unlocked position, the delivery member guard 21' has moved into the proximal position. In a preferred example, the latch 22' is rotatable or linearly movable, in the direction transverse to the longitudinal axis, related to the body 20 after the lock member 23; 23' is in the unlocked position, the delivery member guard 21' has moved into the proximal position. The latch 22' comprises a guide track 223' and the delivery member guard 21' comprises a protrusion 215' protruding into the guide track 223'. The guide track 223' comprises a turning ledge extending both in the direction transverse to the longitudinal axis L and the direction of the longitudinal axis L. The guide track 223' comprises a locking tab 225' comprising a distally directed surface. The latch 22' further comprises a blocking ledge 226' comprises a proximally directed surface. As shown in FIG. 17A, the protrusion 215' of the delivery member guard 21' is positioned in a first position of the guide track 223' when the lock member 23; 23' is in the lock position. FIG. 17B illustrates that the protrusion 215' of the delivery member guard 21' moves into a second position of the guide track 223' after the lock member 23; 23' is in the unlocked position, the delivery member guard 21' has moved into the proximal position. When the protrusion 215' of the delivery member guard 21' moves from the first position of the guide track 223' in to the second position of the guide track 223' along the turning ledge, therefore rotates or linearly moves, in the direction transverse, the latch 22' related to the delivery member guard 21'.

As shown in FIG. 17C, the protrusion 215' of the delivery member guard 21' moves into a third position of the guide track 223' during the delivery operation. When the protrusion 215' of the delivery member guard 21' moves into the third position of the guide track 223', the protrusion 215' of the delivery member guard 21' will be blocked by the both the distally directed surface of the locking tab 225' and the proximally directed surface of the latch 223'. Therefore, the distal movement of the delivery member guard 21' and the latch 22' will be blocked by the distal lid 25' when the delivery operation is finished.

It should be noted that the delivery member guard lock-out mechanism may be crucial in some cases from a medicament delivery device regulation aspect; but is not from a mechanical perspective—the disclosed delivery member guard lock-out mechanism is only an optional feature to the applied present disclosure. There are many known variations of the delivery member guard lock-out mechanism that can be implemented to the sub-assembly of the present disclosure without any substantial modification of the sub-assembly.

The presently disclosed concept has mainly been described above with reference to a few examples. However, as is readily appreciated by a person skilled in the art, other embodiments than the ones disclosed above are equally possible within the scope of the presently disclosed concept, as defined by the appended claims.

The invention claimed is:

1. A sub-assembly for a medicament delivery device cassette unit, the sub-assembly comprising:

a body extending along a longitudinal axis (L) from a proximal end to a distal end, the body comprising:

an inner body for accommodating a medicament container;

an outer shell; and a protrusion with a proximally extending surface, the protrusion extending radially relative to the longitudinal axis (L);

a delivery member guard coaxially attached to the body and being axially movable relative to the body along the longitudinal axis (L);

the delivery member guard comprises an arm with a distally directed surface facing a corresponding proximally directed surface of the protrusion of the body, wherein the arm is flexible in the radial direction relative to the longitudinal axis (L);

a latch adjacent to the delivery member guard and axially movable relative to the body;

wherein at least a part of the delivery member guard and the latch are radially arranged between the inner body and an inner surface of the outer shell; and a lock member attached to the body;

wherein the lock member is movable relative to the latch between a locked position and an unlocked position;

wherein the lock member comprises a distally directed surface facing a proximally directed surface of the latch in the locked position; wherein the distally directed surface of the lock member is further apart from the proximally directed surface of the latch in the unlocked position than in the locked position; and wherein the protrusion with the proximally directed surface protrudes from an outer surface of the inner body;

wherein the latch comprises a radially directed surface facing a corresponding radially directed surface on the arm of the delivery member guard, so that when the lock member is in the locked position, the latch is restricted from moving in the proximal direction relative to the body, and wherein when the lock member is in the unlocked position, the latch is able to move in the proximal direction relative to the body, thereby providing space for the delivery member guard to travel in the distal direction by allowing the flexible arm to travel in the axial direction by moving axially past the radially directed surface of the latch and then moving radially past the protrusion of the body.

2. The sub-assembly for a medicament delivery device cassette unit as claimed in claim 1, wherein the delivery member guard is partially arranged within the body.

3. The sub-assembly for a medicament delivery device cassette unit as claimed in claim 1, wherein the latch is radially, relative to the longitudinal axis (L), arranged between the body and the delivery member guard, and the latch is axially movable relative to the delivery member guard in a proximal direction.

4. The sub-assembly for a medicament delivery device cassette unit as claimed in claim 3, wherein the latch comprises a distally directed surface adjacent to a proximally directed surface of the delivery member guard.

5. The sub-assembly for a medicament delivery device cassette unit as claimed in claim 1, wherein the sub-assembly comprises a biasing member arranged between a distally directed surface of the delivery member guard and a proximally directed surface of the body.

6. The sub-assembly for a medicament delivery device cassette unit as claimed in claim 1, wherein the distally directed surface of the arm of the delivery member guard is spaced apart from the proximally directed surface on the protrusion of the body when the delivery member guard is in a proximal position.

7. The sub-assembly for a medicament delivery device cassette unit as claimed in claim 1, wherein the lock member is rotatable around the longitudinal axis (L) relative to the body between the locked position and the unlocked position.

8. The sub-assembly for a medicament delivery device cassette unit as claimed in claim 7, wherein the lock member comprises a helical distally directed surface; and wherein the distally directed surface of the lock member is a part of the helical distally directed surface.

9. The sub-assembly for a medicament delivery device cassette unit as claimed in claim 8, wherein the helical distally directed surface comprises a distal end and a proximal end; wherein the distal end of the helical distally directed surface is adjacent to the proximally directed surface of the latch when the lock member is in the locked position; and wherein the proximally directed surface of the latch is configured to rotate, relative to the lock member, from the distal end of the helical distally directed surface towards a proximal end of the helical distally directed surface when the lock member is rotated from the locked position to the unlocked position.

10. The sub-assembly for a medicament delivery device cassette unit as claimed in claim 7, wherein the body comprises a bayonet connection on an outer surface of the body for attachment to a part of a medicament delivery device.

11. The sub-assembly for a medicament delivery device cassette unit as claimed in claim 10, wherein the lock member comprises a flange; wherein the flange protrudes from the outer surface of the body; and wherein the flange is aligned with the bayonet connection of the body in the longitudinal direction.

12. A medicament delivery device comprising:

a medicament delivery device cassette unit for accommodating a medicament container;

wherein the medicament delivery device cassette unit comprises the sub-assembly as claimed in claim 1; and a medicament delivery device drive unit releasably attached to the medicament delivery device cassette unit;

wherein the medicament delivery device drive unit comprises a driver for actuating the medicament contained in the medicament container accommodated by the medicament delivery device cassette unit.

13. A sub-assembly for a medicament delivery device cassette unit, the sub-assembly comprising:

a body extending along a longitudinal axis (L) from a proximal end to a distal end and having a protrusion extending radially relative to the longitudinal axis (L), wherein the body comprises an inner body for accommodating a medicament container; an outer shell; and a protrusion with a proximally extending surface, the protrusion extending radially relative to the longitudinal axis (L);

a delivery member guard coaxially attached to the body and being axially movable relative to the body along the longitudinal axis (L) and having two distally extending flexible arms configured to move radially relative to the protrusion;

the delivery member guard comprises an arm with a distally directed surface facing a corresponding proximally directed surface of the protrusion of the body;

a latch adjacent to the delivery member guard and axially movable relative to the body;

wherein at least a part of the delivery member guard and the latch are radially arranged between the inner body and an inner surface of the outer shell; and a lock member attached to the body;

wherein the lock member is movable relative to the latch between a locked position and an unlocked position, wherein the lock member comprises a distally directed surface facing a proximally directed surface of the latch in the locked position; and wherein the distally directed surface of the lock member is further apart from the proximally directed surface of the latch in the unlocked position than in the locked position; and wherein the protrusion with the proximally directed surface protrudes from an outer surface of the inner body;

wherein the latch comprises a radially directed surface facing a corresponding radially directed surface on the arm of the delivery member guard, so that when the lock member is in the locked position, the latch is restricted from moving in the proximal direction relative to the body, and wherein when the lock member is in the unlocked position, the latch is able to move in the proximal direction relative to the body, thereby providing space for the delivery member guard to travel in the distal direction by allowing the flexible arm to travel in the axial direction by moving axially past the radially directed surface of the latch and then moving radially past the protrusion of the body.

14. The sub-assembly of claim 13, wherein the latch is axially movable relative to the delivery member guard in a proximal direction and has a distally directed surface adjacent to a proximally directed surface of the delivery member guard.

15. The sub-assembly of claim 13, wherein the lock member is rotatable around the longitudinal axis relative to the body between the locked position and the unlocked position.

16. The sub-assembly of claim 13, wherein a spring biases the delivery member guard in the proximal direction.

17. The sub-assembly of claim 13, wherein a helical distally directed surface on the lock member comprises a distal end and a proximal end, where the distal end of the helical distally directed surface is adjacent to the proximally directed surface of the latch when the lock member is in the locked position and where the proximally directed surface of the latch rotates relative to the lock member from the distal end of the helical distally directed surface towards a proximal end of the helical distally directed surface when the lock member is rotated from the locked position to the unlocked position.

* * * * *